United States Patent [19]
Pick et al.

[11] Patent Number: 5,330,722
[45] Date of Patent: Jul. 19, 1994

[54] GERMICIDAL AIR FILTER

[75] Inventors: William E. Pick, Carp, Canada; Kerby F. Fannin, Jerome, Mich.

[73] Assignee: William E. Pick, Carp, Canada

[21] Appl. No.: 950,833

[22] Filed: Sep. 24, 1992

Related U.S. Application Data

[63] Continuation-in-part of Ser. No. 661,251, Feb. 27, 1991, abandoned.

[51] Int. Cl.$^5$ .......................... A61L 2/00; B01D 41/00
[52] U.S. Cl. ...................... 422/121; 55/279; 96/16; 96/55; 250/436; 250/438; 250/492.1; 250/504 R
[58] Field of Search ............. 422/121, 22, 24; 55/6, 55/102, 124, 279; 250/436, 438, 492.1, 504 R; 95/63, 68, 277, 278; 96/15, 16, 55

[56] References Cited

U.S. PATENT DOCUMENTS

| | | | |
|---|---|---|---|
| 3,798,879 | 3/1974 | Schmidt-Burbach et al. | 55/102 |
| 4,087,925 | 5/1978 | Bienek | 422/24 |
| 4,121,107 | 10/1978 | Bachmann | 250/492.1 |
| 4,449,050 | 5/1984 | Kamhi | 422/24 |
| 4,786,812 | 11/1988 | Humphreys | 422/24 |
| 4,896,042 | 1/1990 | Humphreys | 250/504 R |
| 4,978,372 | 12/1990 | Pick | 55/132 |
| 5,138,175 | 8/1992 | Kim et al. | 250/504 R |

Primary Examiner—Robert J. Warden
Assistant Examiner—L. M. Crawford
Attorney, Agent, or Firm—James D. Hall

[57] ABSTRACT

A germicidal air purifier for trapping and destroying airborne microorganisms is disclosed. The air purifier includes an ultraviolet radiation source and a juxtaposed filter medium. A one of the ultraviolet radiation source and the filter medium is fixed and the other is displaceable so that at least an upstream side of the filter medium is systematically exposed to germicidal levels of radiation. In a first preferred embodiment, a fixed ultraviolet lamp irradiates a cylindrical air filter which is rotated on its longitudinal axis in close proximity to the lamp so that the upstream side of the filter is systematically irradiated. In a second preferred embodiment, a radiant lamp fixture is moved reciprocally across an upstream side of a planar filter to systematically irradiate the filter. In a third preferred embodiment, a radiant lamp fixture is rotated about an axis which is orthogonal to its longitudinal midpoint so that a circular area of a planar filter is irradiated. The advantage is that microorganisms trapped on the filters are exposed to a lethal dose of radiation and the air purifier is consistently effective at destroying a significant percentage of airborne microorganisms suspended in air passed through the filter.

17 Claims, 12 Drawing Sheets

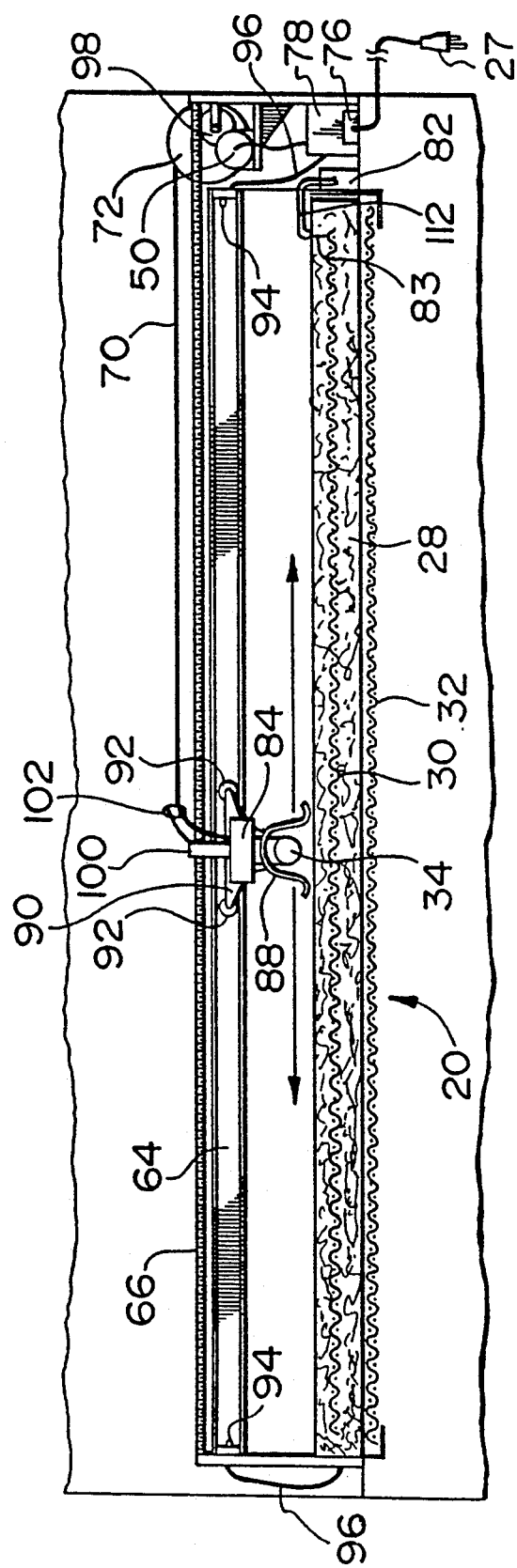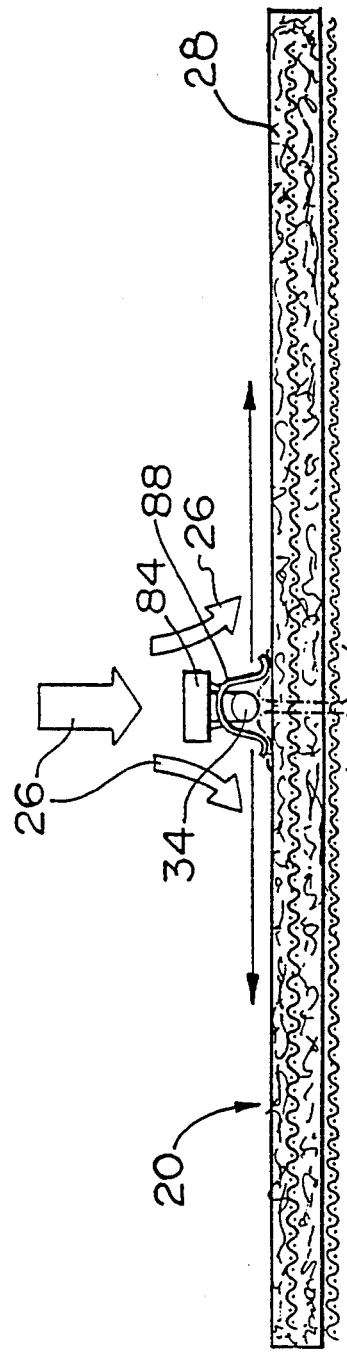

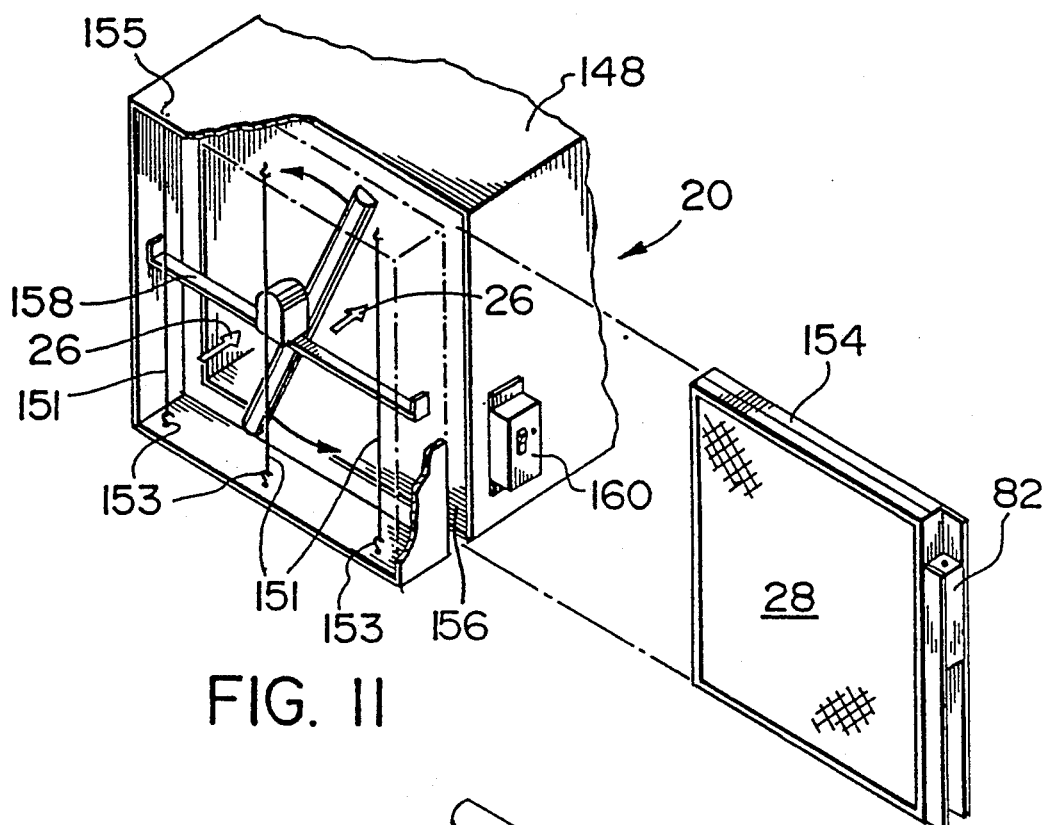
FIG. 11
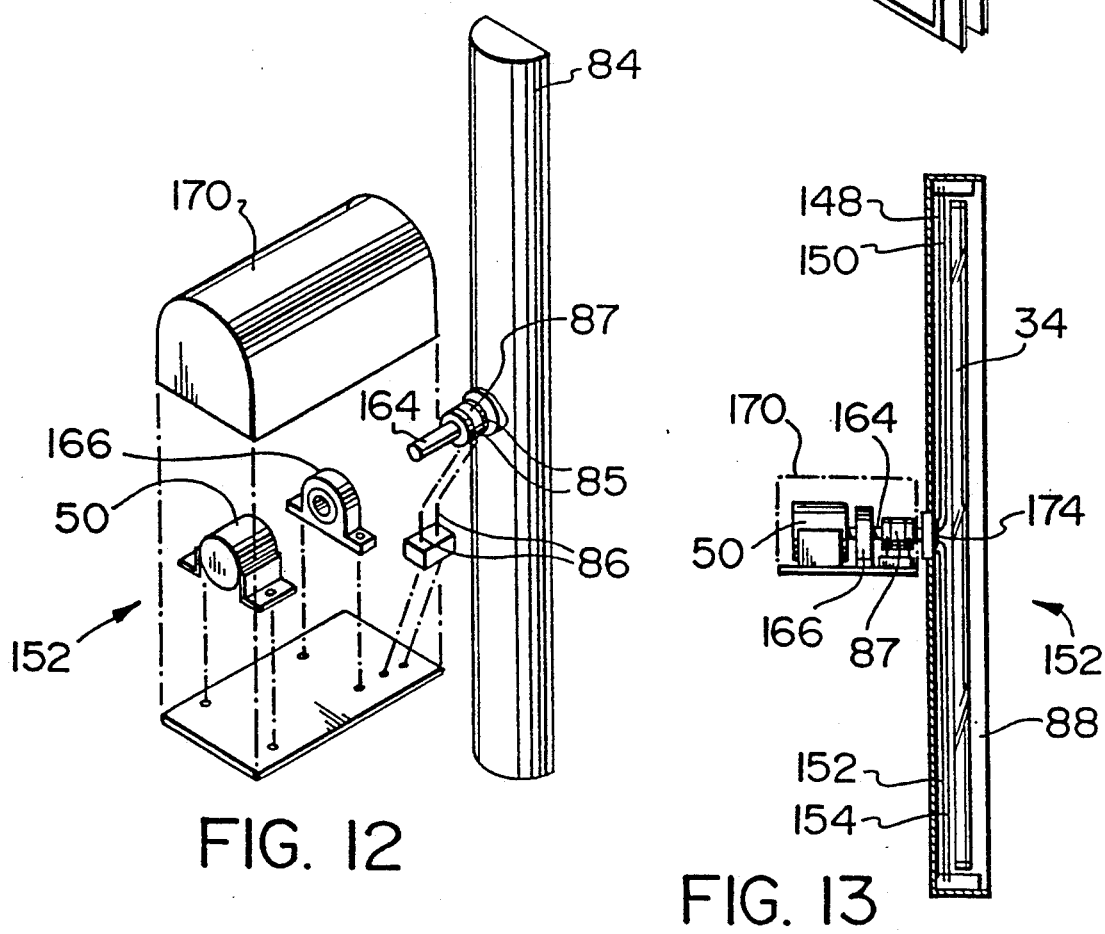
FIG. 12
FIG. 13

GERMICIDAL AIR FILTER

RELATED APPLICATIONS

This application is a continuation-in-part of U.S. patent application No. 07/661,251 filed Feb. 27, 1991, and now abandoned.

FIELD OF THE INVENTION

The present invention relates to air purification and in particular to air purification by filtration and irradiation with an ultraviolet radiation source.

BACKGROUND OF THE INVENTION

The airborne transmission of disease organisms, especially respiratory disease organisms has long been recognized as a serious problem in health care. With a growing population of immune deficient individuals due to the contraction of acquired immune deficiency syndrome (AIDS) and other debilitating conditions which weaken the immune system, the control of airborne disease transmission has become increasingly important and difficult. Air purification is perceived to be the only practical method of controlling airborne disease transmission. The increasing incidence of contraction of tuberculosis, pneumonia and other airborne disease in modern health institutions indicates, however, that known air purification systems are inadequate in controlling the spread of airborne microorganisms.

Air purification by means of filtration and irradiation are widely practiced. Traditional air treatment systems are commonly arranged in an order of filtration, irradiation and humidification. Irradiation is placed after filtration because the ultraviolet lamps used for that purpose readily attract dust which can accumulate on a surface of the lamp and interfere with their germicidal effect by absorbing and/or reflecting radiant energy. Irradiation is placed before humidification because ultraviolet radiation is most effective in a relatively dry atmosphere which promotes oxidation.

The germicidal effects of light rays of short wavelength has been recognized for more than half a century. A diverse array of methods and apparatus have been invented for irradiating fluids, and air in particular, in order to control the spread of microorganisms by destroying those microorganisms suspended in the fluid. The ultraviolet radiation for it's germicidal effect:

| | |
|---|---|
| 2,070,307 - Nicholls | 3,757,496 - Sievers |
| 2,248,618 - Fischer | 4,017,736 - Ross |
| 2,279,810 - Arnott | 4,694,179 - Lew et al. |
| 2,628,083 - Rense | 4,750,917 - Fujii |
| 3,518,046 - Circirello | 4,806,768 - Keutenedjian |
| 3,576,593 - Circirello | |

Ultraviolet radiation has been proven to be more effective and economically feasible than any other approach to reducing the density of airborne microorganisms in an enclosed space. Two principle methods of utilizing ultraviolet radiation to destroy airborne microorganisms include air duct irradiation and the direct irradiation of the upper air in living or working areas. Although several studies have demonstrated convincingly that ultraviolet radiation can effectively reduce the density of airborne microorganisms, in practice wide variations in effectiveness have been documented.

Traditionally, air purification systems have relied on exposure of airborne microorganisms to ultraviolet radiation by passing air over or around one or more ultraviolet lamps. All of the patent references listed above relate to some variation on this method. The method has two principle shortcomings. First, exposure time depends almost exclusively on the rate of air flow around the lamps. Second, it is well known that ultraviolet radiation is readily adsorbed by most surfaces. As a result, accumulations of dust and particulates on radiant lamps adversely affects their germicidal effectiveness. Since the operation of radiant lamps generates an electrostatic field, they readily attract and accumulate particulate matter when placed directly in a flow of air, especially if the flow of air is unfiltered or poorly filtered. These factors may account in part for the variable results experienced to date with the use of ultraviolet irradiation in controlling the density of airborne microorganisms.

Although most microorganisms, including bacteria and viruses, are readily destroyed by sufficient exposure to ultraviolet radiation, the duration of exposure required to destroy a microorganism depends on a number of variable factors including humidity, the particle density in the air being treated and distance of a microorganism from a source of radiation.

Several important factors have been largely ignored in prior art disclosures for purifying air by destroying airborne microorganisms using ultraviolet radiation. It is well known that the strength of radiation decreases inversely with the square of the distance from a radiation source. Ultraviolet radiation is therefore most effective at close range. Relatively long exposure times may be required to destroy certain microorganisms, especially in humid environments. Host importantly, in order to ensure adequate radiation exposure microorganisms are preferably trapped on a filter surface before or during exposure, thus ensuring radiation levels and exposure times which are adequate to effect their destruction. Finally, radiation lamps must be protected from accumulating airborne particulate matter which can reflect and/or absorb radiation.

U.S. Pat. No. 4,694,179 entitled Symbiotic Filter-Sterilizer which issued Sep. 15, 1987 to Lew et al. teaches a cylindrical filter structure which surrounds, or is surrounded by, one or more ultraviolet lamps. The ultraviolet lamps are in turn encased in clear plastic tubes to protect the lamp(s) from fluids to be filtered. Although this invention appears to espouse some of the principles outlined above, it suffers from several shortcomings. First, the recommended filter is a porous filter through which most microorganisms pass unimpeded. Radiation exposure time is therefore random and dependent on the rate of fluid flow. Second, the transparent tubes which protect the lamps are exposed directly to fluids passed through the porous filter. The tubes therefore collect fine particulates which are resistant to ultraviolet radiation and absorb or reflect the radiation so that the effectiveness of the irradiation of the filter degrades with time. Third, the relationship between the fibers of the porous filter and the ultraviolet lamp is static. The fibers of the porous filter exposed to direct radiation therefore shade the areas of the filter not directly exposed. These "shaded" areas can provide pockets where microorganisms survive under the right conditions.

The prior art therefore suffers from several disadvantages which can be improved upon.

SUMMARY OF THE INVENTION

It is an object of the present invention to provide a germicidal air filter which effectively destroys airborne microorganisms suspended in air to be purified.

It is another object of the invention to provide a germicidal air filter that destroys microorganisms by trapping the organisms on an air filter surface which is exposed to germicidal levels of ultraviolet radiation.

It is a further object of the invention to provide a germicidal air filter wherein an ultraviolet radiation source and a filter medium are displaceable with respect of one to the other so that an entire surface of the filter is systematically exposed to intense radiation.

It is a further object of the invention to provide an electrostatically enhanced germicidal air filter.

It is yet a further object of the invention to provide an electrostatically enhanced germicidal air filter which removes ozone generated by the ultraviolet radiation source from the filtered air.

The invention therefore provides a germicidal air filter comprising a filter medium for removing particulate matter including at least a portion of microorganisms from an air stream to be filtered, the filter medium having an upstream side exposed to the air to be filtered, at least one germicidal radiation source located in proximity to the upstream side of the filter medium and arranged for exposing at least a portion of that side of the filter medium to ultraviolet radiation, one of the radiation source and the filter medium being displaceable with respect one to another and means for displacing the one of the radiation source and the filter medium so that a surface of the upstream side of the filter medium is systematically and repeatedly exposed to germicidal levels of ultraviolet radiation.

In accordance with a preferred embodiment of the invention, the filter medium is electrostatically enhanced so that a greater percentage of particulate matter is collected from air filtered and the particulate matter that is collected includes particles that are significantly smaller in size than can be collected by a similar filter medium which is not electrostatically enhanced. Electrostatic air filtration systems are well known for removing very fine particles from an air stream. By electrostatically enhancing an air filter the capture rate of airborne microorganisms is enhanced and consequently the destruction of microorganisms is facilitated.

In a first embodiment of the invention a cylindrical filter is rotated around a longitudinal axis to expose a surface of the filter to germicidal radiation emitted by an ultraviolet radiation source positioned adjacent a side of the filter. The ultraviolet radiation source is preferably a lamp which may be an ozone producing lamp, the ozone produced further facilitating the destruction of microorganisms. The ultraviolet lamp is preferably isolated from the air flow stream so that dust suspended in the air to be filtered does not accumulate on a surface of the lamp and thereby inhibit the irradiation. A parabolic reflector having a focal point which coincides with the longitudinal axis of the cylindrical filter is preferably provided so that radiation emitted by a side of the lamp remote from the filter is directed back to the surface of the filter.

In a second embodiment of the invention, a planar filter is associated with an ultraviolet radiation source which is moved reciprocally across the filter surface to systematically and repeatedly expose the surface to radiant energy. In this embodiment, the ultraviolet radiation source is also protected from direct exposure to air to be filtered by a reflector which is suspended over the radiation source in close proximity to the filter surface. The reflector deflects air away from the radiation source, which is preferably a lamp, and creates a partial vacuum around the lamp which helps prevent an exposure of the lamp to dust laden air, thereby prolonging the periods between maintenance and the effectiveness of the lamp as a germicidal radiation source.

In a third embodiment of the invention, a planar filter is exposed to radiation by an ultraviolet radiation source that is rotated in close proximity to the filter about an axis which is at a right angle to a longitudinal axis of the radiation source. The rotation of the radiation source, preferably an ultraviolet lamp, may be driven by an electric motor which rotates a shaft that supports the lamp, or by air flow through the filter. In the latter case, the lamp is balanced and the shaft is driven by propeller-shaped blades oriented at opposite angles. The lamp is likewise preferably shielded from direct contact with air to be filtered by a reflector which also reflects radiant energy onto the filter surface and creates a partial vacuum around the lamp which helps prevent an exposure of the lamp to dust laden air.

Any embodiment of the germicidal air filter in accordance with the invention may further include one or more ultraviolet radiation sources located adjacent a downstream side of the filter for destroying microorganisms which are trapped deep in the filter medium adjacent that side of the filter.

The germicidal effect of the germicidal air filter in accordance with the invention may also be optionally enhanced, when appropriate, by the generation of ozone to promote the oxidation of organic matter trapped by the filter medium. Ozone can be generated by using an ozone-generating ultraviolet lamp and/or by arranging one or more corona wires upstream of the filter, which wires generate ozone when charged with high voltage, low amperage electric current.

Experimentation has shown that a germicidal air filter in accordance with the invention effectively destroys airborne microorganisms and that an enclosed space can be substantially ridded of airborne microorganisms using an appropriately sized air filter(s) in accordance with the invention.

BRIEF DESCRIPTION OF THE DRAWINGS

The invention will now be explained by way of example only and with reference to the following drawings wherein:

FIG. 8 is a cross-sectional view taken along lines 8—8 of the germicidal air filter shown in FIG. 7;

FIG. 9 is a schematic cross-sectional view of the filter shown in FIG. 7, illustrating an air flow path created by an ultraviolet lamp shielded with a reflector in accordance with the invention.

FIG. 11 is an exploded perspective view of a third embodiment of the invention installed in an air duct of an air handling system;

FIG. 12 is an exploded perspective view of a drive and electric power transmission arrangement for the germicidal air filter shown in FIG. 11;

FIG. 13 is a cross-sectional side view of the apparatus shown in FIG. 12;

DETAILED DESCRIPTION OF THE PREFERRED EMBODIMENT

The present invention provides a germicidal air filter, generally referred to by reference 20, which includes a filter for trapping and removing particulate matter from an air stream, including at least a portion of the microorganisms suspended in the air stream, and an ultraviolet radiation source for destroying microorganisms trapped by the filter. In order to ensure adequate and efficient exposure of the filter surface to the ultraviolet radiation, one of the ultraviolet source and the filter medium are movable with respect to one another. If the ultraviolet source is fixed, the filter medium is systematically and repeatedly moved across a field of radiation generated by the source. If the filter medium is fixed, then the ultraviolet source is systematically and repeatedly moved across the filter in a predetermined pattern. Thus, controlled irradiation of the filter surface is ensured. Movement of the radiation source/filter medium also promotes deeper and more thorough irradiation of the filter because the changing angle of incidence of radiation on the filter substantially eliminates shaded areas which naturally occur when a fibrous material such as a filter medium is irradiated with a radiation source that is located in a fixed position relative to the filter.

Figure 1:
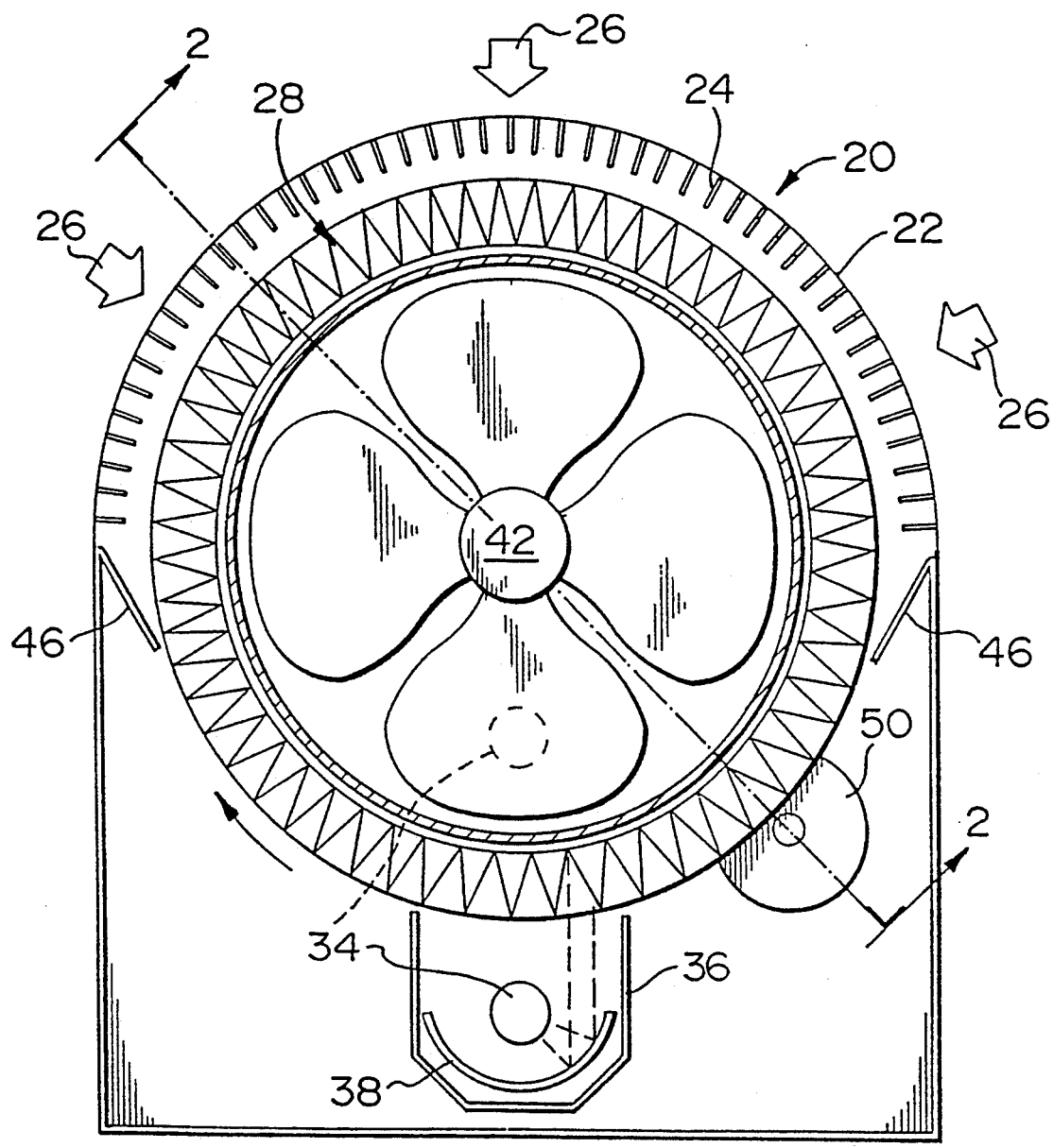
FIG. 1 is a top plan view of a first preferred embodiment of the invention showing a germicidal air filter with a cover of the filter cabinet removed to expose the filter components.

FIG. 1 is a top plan view of a first preferred embodiment of a germicidal air filter in accordance with the invention. The germicidal air filter 20 includes a cabinet 22 which is illustrated in this figure with a cover 23 (See FIG. 6) removed. The cabinet includes louvers 24 for admitting air to be filtered, schematically illustrated by arrows 26. Air is drawn through louvers 24 by a fan 42 which draws the air through a cylindrical filter generally indicated by reference 28. The filter medium 28 is rotated on an axis by a drive means 50, as will be explained in more detail with reference to FIGS. 2-4. The filter 28 is preferably a pleated paper filter medium suitable for air filtration. Other filter materials such as fiberglass, polymer fibers and the like may also be used. The purpose of the filter is to trap particulates suspended in the air to be filtered 26 and to expose the particulates thus trapped to ultraviolet radiation which is generated by an ultraviolet lamp 34. One or more ultraviolet lamps 34 (shown in phantom lines) may also be provided on the downstream side of the cylindrical filter medium 28 to destroy microorganisms which penetrate deeply into the filter medium.

In order to minimize an accumulation of dust contamination on the ultraviolet lamp 34 located on the upstream side of the filter, it is protected by baffles 46 located on opposite sides of the cylindrical filter 28 which prevent most air to be filtered 26 from entering a rear side of the housing 22. The ultraviolet lamp 34 is further shielded by a housing 36 which surrounds the lamp. In order to increase the efficiency of irradiation a parabolic reflector 38 is provided for redirecting radiation emitted from a side and rear of the ultraviolet lamp 34, to the filter surface. The parabolic reflector 38 is preferably shaped so that it has a focal point which coincides with the axis of the cylindrical filter medium 28, thus ensuring that as much radiation as possible is concentrated on the surface of filter medium 28. If filter 28 is a pleated filter as shown in FIG. 1, parabolic reflector 38 with a focal point coincident with the axis of the cylindrical filter medium 28 also ensures that the pleats of the cylindrical filter 28 are each exposed to radiation since the reflected radiation impinges directly on a side of each pleat within the bounds of housing 36.

Figure 2:
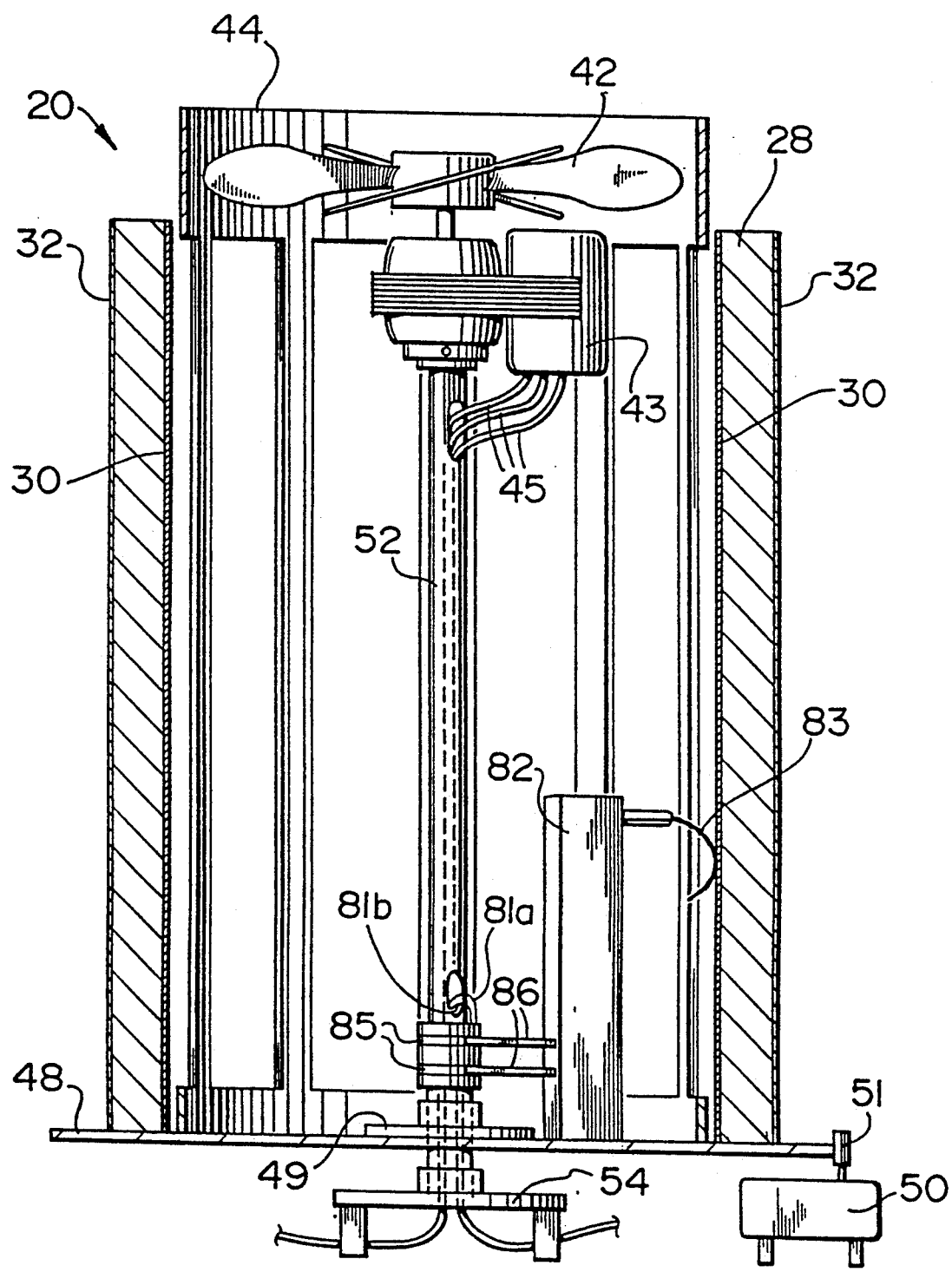
FIG. 2 is a vertical cross-sectional view taken along lines 2—2 of the air filter shown in FIG. 1, illustrating the drive and power components of the air filter.

FIG. 2 is a cross-sectional view of the filter and mechanical drive portion of the germicidal air filter 20 shown in FIG. 1. The cylindrical filter 28 is supported by a filter medium support drum 44 on a rotatable disc or turntable 48 which is affixed to a support bracket 49 that is rotatably supported on a stationary base 54. The support bracket 49 has an axial bore which accommodates a stationary post 52. The stationary post 52 supports a fan 42 and the fan motor 43. It is therefore apparent that the cylindrical filter medium 28 rotates around the fan 42 which is mounted to the top of the stationary post 52. The turntable 48 is rotated by a drive means 50 which may be a stepper motor, a geared motor, or an electric solenoid driven rachet or the like. A drive spindle 51 is conveniently a rubber coated shaft which drives turntable 48 by frictional engagement with a periphery of the turntable. A belt drive or the like may also be used. The fan motor 43 is powered by electrical conductors 45 which run up through the stationary post 52 and exit an opening cut in the side of the stationary post. The cylindrical filter medium 28 is preferably electrostatically enhanced so that it traps a maximum number of microorganisms from air passing therethrough. Electrostatically enhanced air filters of the charged media type are well known in the art. In accordance with the preferred construction, a grounded or negatively charged electrically conductive charging medium 32 surrounds an outside surface of the cylindrical filter medium 28. The grounded charging medium 32 may be an expanded aluminum mesh or the like which is preferably affixed to the cylindrical filter medium 28 at the time of manufacture and is disposable therewith. A positively charged electrically conductive charging medium 30 is preferably permanently affixed to the filter support drum 44. Charging medium 30 may be a welded wire mesh, a metallic screen or the like. Alternatively, the charging medium 30 may be a carbon impregnated open celled plastic foam which is electrically conductive. Foam of this type not only serves as an effective electrostatic charging medium but if properly maintained, it also scrubs the filtered air of ozone produced by ultraviolet lamp(s) 34 (See FIG. 1). In the instance where charging medium 30 is an open celled foam impregnated with fine carbon or activated charcoal particles it is preferable that the charging medium 30 is affixed to and likewise disposable with the cylindrical filter medium 28. An electrical connection is made with the grounded charging medium 32 by contact with turntable 48 which is preferably a conductive metal such as aluminum. In order to ensure good contact, charging medium 32 is preferably cut somewhat longer than the cylindrical filter medium 28 and bent around the bottom corner of the cylindrical filter medium 28 so that contact with turntable 48 is ensured. If the turntable 48 is manufactured from a plastic or other non-conductive substance, a grounding shoe (not illustrated) must be connected to a suitable ground and positioned so that charging medium 32 contacts the grounding shoe when the cylindrical filter medium 28 is installed in the germicidal air filter 20.

In order to electrostatically enhance the cylindrical filter medium 28, a high voltage electrical current must be applied to charging medium 30 to create an electrostatic field between the positive charging medium 30 and the grounded charging medium 32. The electrostatic field polarizes the fibers of the cylindrical filter medium 28 so that the fibers positively attract particulate matter suspended in air passed therethrough, thereby enhancing the capacity of the filter to capture small airborne particulates including microorganisms. Since cylindrical filter medium 28 rotates around stationery post 52, special provisions for supplying high voltage to charging medium 30 must be provided. In the preferred embodiment of the invention shown in FIGS. 2 through 6, the charging medium 30 is supplied with high voltage, low amperage current from a high voltage power supply 82 which is mounted to turntable 48. The high voltage power supply 82 has a positive pole which is connected to a high voltage electrode 83 that is positioned to make electrical contact with the charging medium 30. The high voltage power supply operates on current supplied by a transformer 78 (See FIG. 5), transformer 78 transforms mains power to 24 volts which is converted by high voltage power supply 82 to low amperage, high voltage current on an order of 10 kv. The 24 volt power is conducted from transformer 78 to high voltage power supply 82 by electrical conductors 81a and 81b which are respectively connected to electrically conductive ring contactors 85. A pair of electrically conductive brushes 86 respectively contact the ring contactors 85 and thereby supply electrical power to high voltage power supply 82 as will be explained in more detail with reference to FIG. 4.

Figure 3:
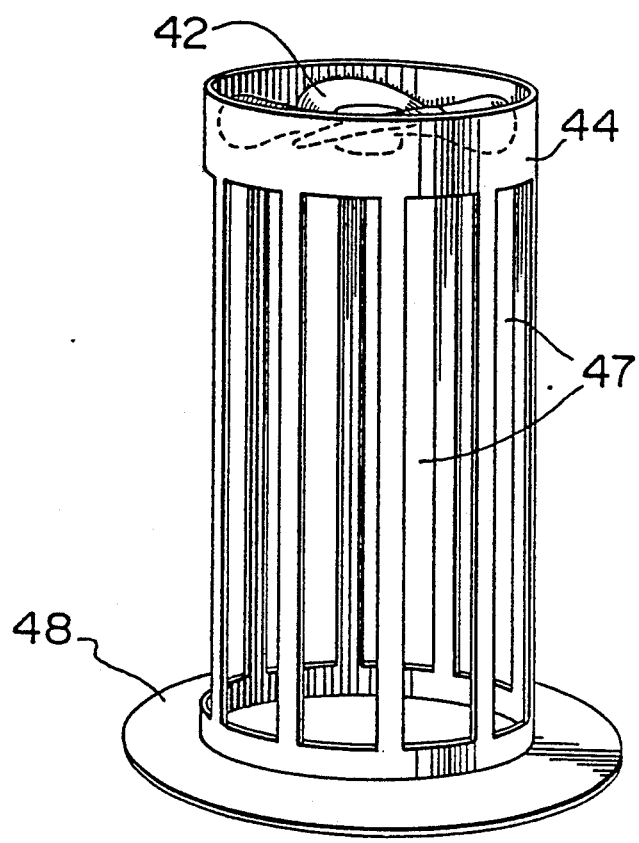
FIG. 3 is a perspective view of a filter support drum for the germicidal air filter shown in FIG. 1.

FIG. 3 shows a perspective view of the filter support drum 44. The filter support drum is preferably a lightweight plastic cylinder having slots 47 which extend longitudinally of the sidewall of the filter support drum 44, the slots 47 being cut at regular intervals in the sidewall to permit air to be drawn through the cylindrical filter medium 28 by fan 42 and expelled through a top of the filter support drum 44. An unslotted rim around the top of the sidewall of the filter support drum 44 provides a shroud for fan 42.

Figure 4:
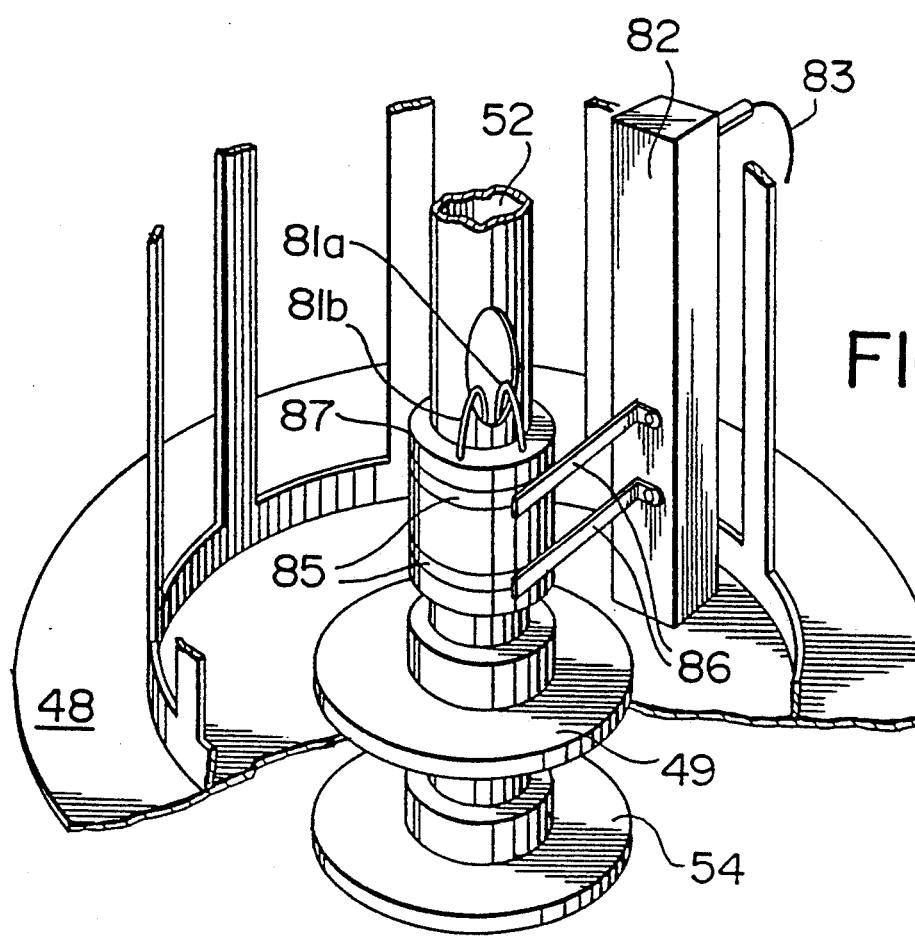
FIG. 4 is a fragmentary view of the mechanisms for rotating the filter support drum shown in FIG. 3 and supplying power to a high voltage power supply for electrostatically enhancing the germicidal air filter shown in FIG. 1.

FIG. 4 shows an enlarged portion of the filter and mechanical drive illustrated in FIG. 2. As explained above, turntable 48 rotates around the stationery post 52. High voltage power supply 82 is affixed to turntable 48 and rotates therewith. In order to supply operating current to high voltage power supply 82, a pair of electrical conductors 81a and 81b which extend through the fixed post 52 are connected to respective electrically conductive ring contactors 85. The ring contactors 85 are mounted to a cylindrical electrical insulator 87 made of rubber, plastic or the like. A pair of flexible brushes 86 are preferably made of aluminum or brass. The flexible brushes 86 are connected to the input poles of high voltage power supply 82. This arrangement permits high voltage power to be continuously supplied to a charging medium 30 through high voltage electrode 83 (see FIG. 2).

Figure 5:
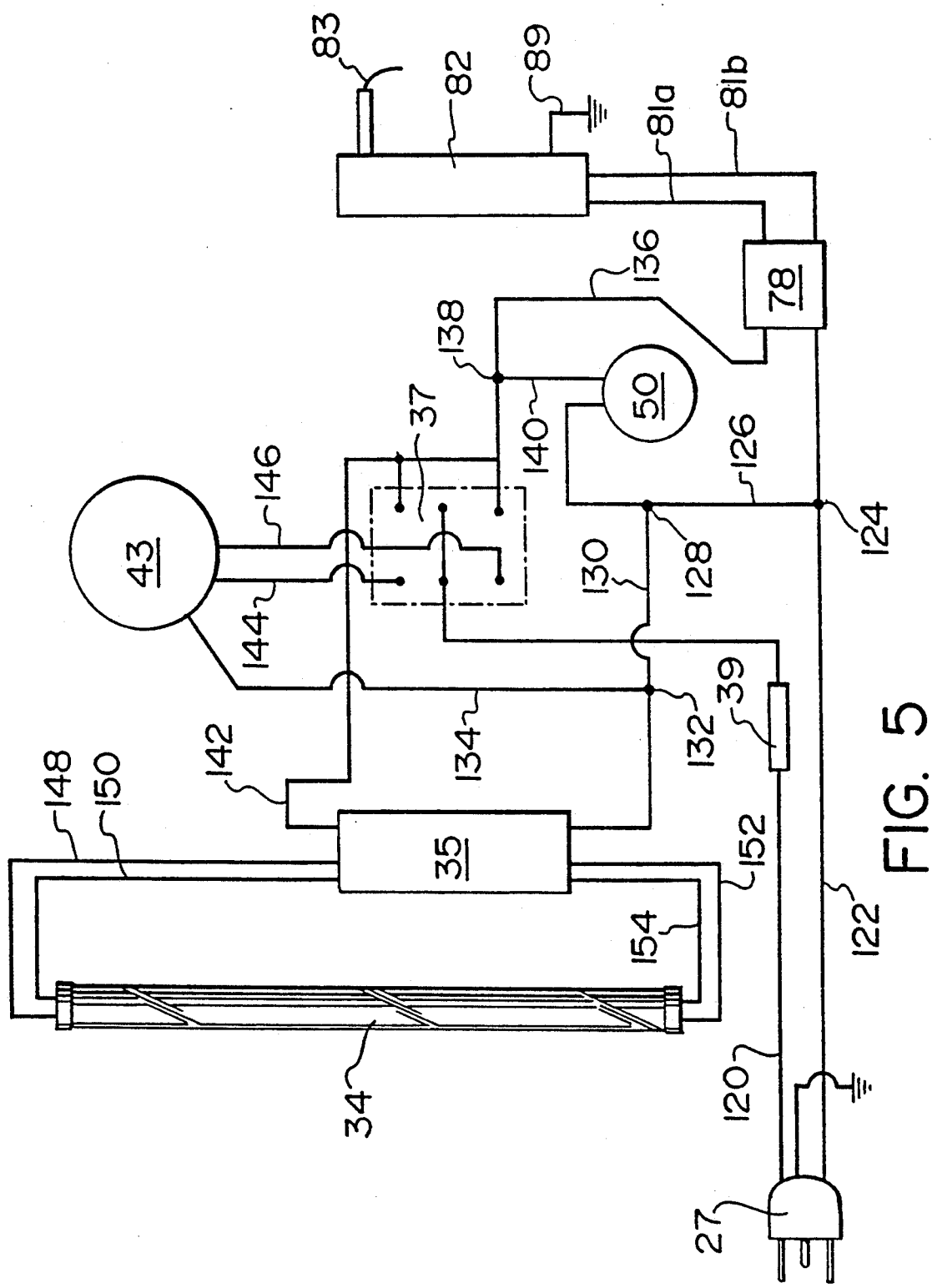
FIG. 5 is a schematic electrical wiring diagram used for connecting the electrical components of the germicidal air filter shown in FIG. 1 to an electrical power source.

FIG. 5 shows a schematic wiring diagram for the germicidal air filter 20 shown in FIGS. 1-4. The germicidal air filter 20 is preferably supplied with electrical current through a 3 pronged connector 27 which may be connected to a standard mains outlet. Conductors 120 and 122 are respectively connected to the positive and negative prongs of three pronged connector 27. Conductor 120 is connected to a fuse 39 for protecting the circuitry of the germicidal air filter 20 from power spikes and the like. Conductor 120 also connects directly to a switch 37 which is preferably a three pole switch having an off position and two operating positions for controlling the fan motor 43, preferably a dual speed fan motor. Conductor 122 is connected to a junction point 124 and to a 24 volt transformer 78. Conductor 126 is likewise connected to junction point 124 as well as junction point 128 and the drive means 50 which may be a geared motor, or a stepper motor or the like. A conductor 130 connects junction point 128 and an ultraviolet lamp ballast 35. Junction point 132 connects conductor 130 and conductor 134 which is connected to the fan motor 43. From switch 37 a conductor 136 is connected to a junction point 138 and to the 24 volt transformer 78. A conductor 140 connects junction point 138 and the drive means 50. A second conductor 142 connects the switch 37 and the ballast 35 for the ultraviolet lamp 34. Conductors 144 and 146 connect switch 37 with the two speed fan motor 43. Conductors 148, 150, 152 and 154 respectively connect the ultraviolet lamp 34 with the ballast 35. Conductors 81a and 8b connect the high voltage power supply 82 with the 24 volt transformer 78. The positive pole of the high voltage power supply is connected to a high voltage electrode 83 and the negative pole of high voltage power supply 82 is connected to a ground 89.

Figure 6:
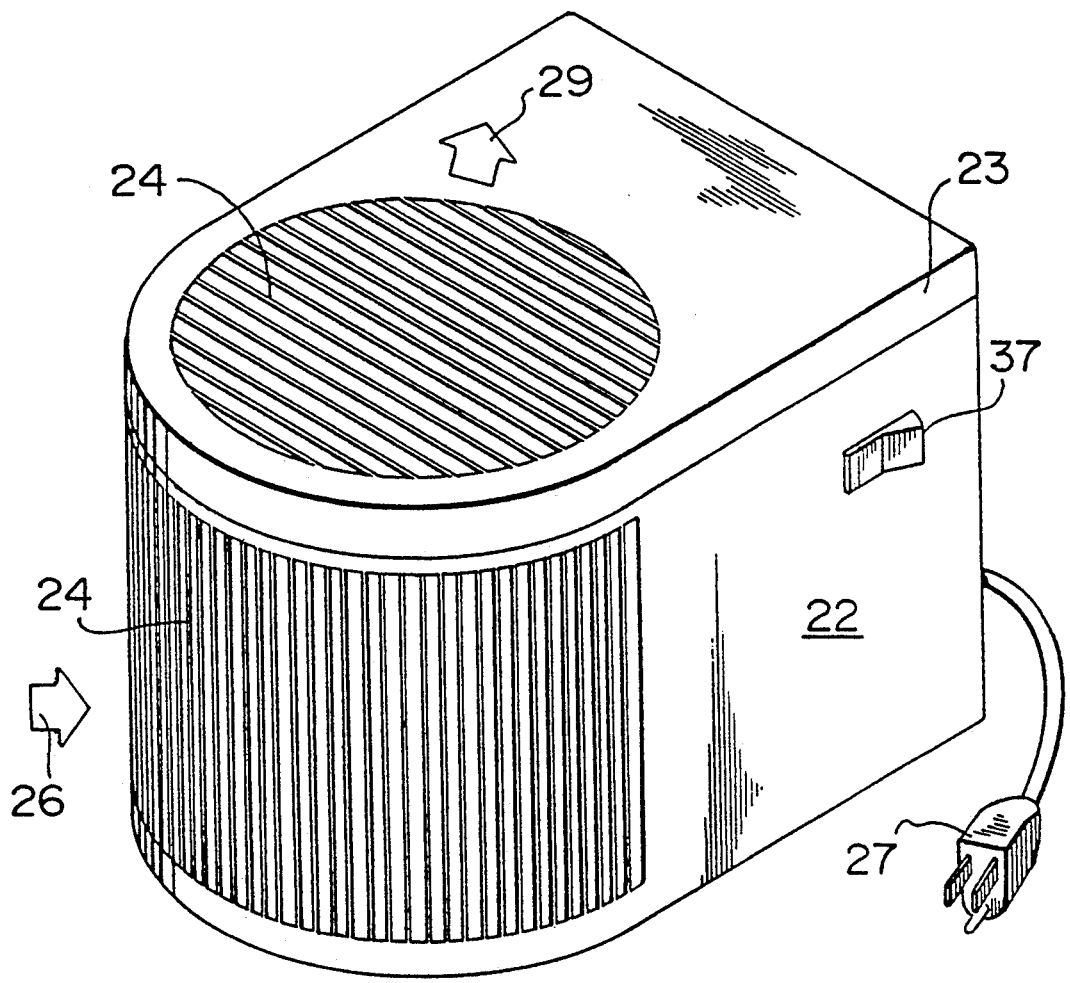
FIG. 6 is a perspective view of a cabinet suitable for use in housing the germicidal air filter shown in FIGS. 1-5.

FIG. 6 shows a cabinet suitable for housing the germicidal air filter 20 shown in FIGS. 1 through 5. The cabinet 22 includes a switch 37 and a power cord having a pronged receptacle 27. A front portion of the cabinet includes louvers 24 to permit the entry of air to be filtered 26. A cover 23 which is hinged on a rear side of the cabinet, lifts upward and rearward to permit access to the interior of the cabinet so that the unit may be serviced by replacing the disposable cylindrical filter medium 28 (See FIG. 2). A top portion of the cabinet likewise includes louvers 24 to permit filtered air 29 to be ejected by fan 42 (See FIG. 2) from the cabinet 22.

Many other cabinet configurations are also suitable for use with the germicidal air filter 20 described above.

FIGS. 7 through 10 illustrate a second embodiment of the germicidal air filter 20. This embodiment is more readily adapted to installation in certain central air handling systems. This embodiment of the invention includes a framework 58 which supports a filter medium 28 in a plane which is conveniently flat. The filter medium 28 may be fiberglass, paper, or a similar filter medium. Filter medium 28 is preferably a dielectric fibrous material which is adapted to electrostatic enhancement. The air filter 20 includes at least one ultraviolet lamp fixture 84 on an upstream side of filter medium 28. The lamp fixture 84 is mounted transversely to the filter medium 28 and is supported by support rails 64 as will be explained in relation to FIG. 8. The ultraviolet lamp fixture 84 is moved reciprocally across the surface of filter medium 28 in order to systematically and repeatedly expose substantially the entire filter surface to ultraviolet radiation. The ultraviolet lamp fixture 84 may be moved across the surface of filter medium 28 by a number of mechanisms well known in the art. In the preferred embodiment, the lamp is moved by means of an elongated threaded drive rod 66 which is turned by a drive means 50, the operation of which will be explained in more detail in relation to FIG. 8. The lamp is powered by a power cord 70 which is preferably retained in a semi-taut condition by a spring loaded take-up reel 72 to prevent the power cord 70 from becoming entangled with the ultraviolet lamp fixture 84 as it reciprocally cycles across the surface of filter medium 28.

Figure 7:
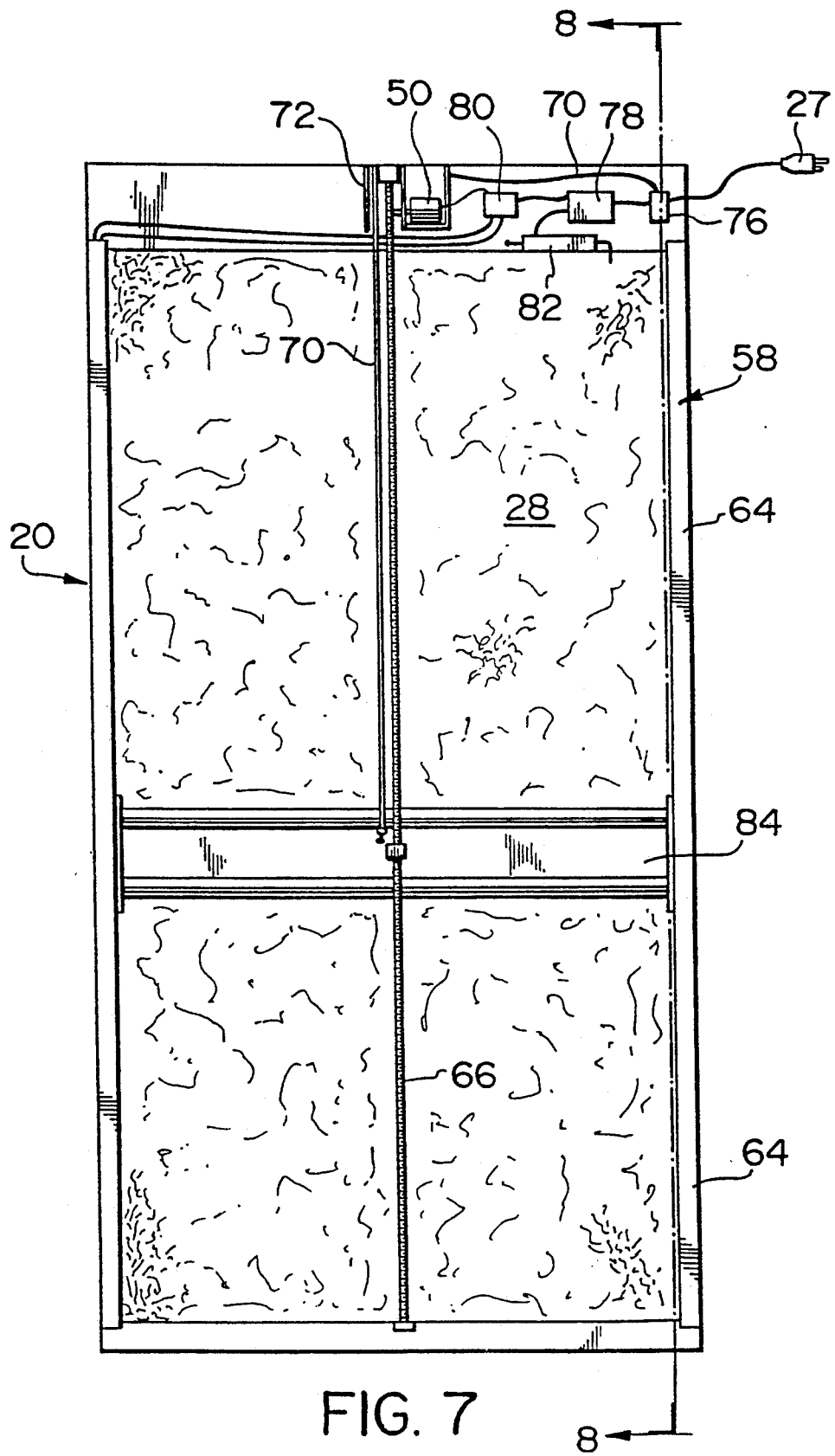
FIG. 7 is a top plan view of a second preferred embodiment of a germicidal air filter in accordance with the invention.

FIG. 8 is a cross-sectional view taken along lines 8—8 of the germicidal air filter 20 shown in FIG. 7. An ultraviolet lamp fixture 84 commonly includes a ballast 35 (see FIG. 10) and an ultraviolet lamp 34. This may be an ozone producing ultraviolet lamp commonly available from a number of manufacturers and well known in the art. The lamp 34 is shrouded by a reflector 88 the function of which is explained in more detail in relation to FIG. 9.

Affixed to each end of lamp fixture 84 is a support bracket 90. The support bracket 90 includes a freely rotatable wheel 92 on each end which runs in a guide rail 64 that is shaped to support it. Affixed to each end of guide rail 64 is a limit switch 94 connected by an insulated electrical conductor 96 to a motor control 80 (See FIG. 7). Each time the ultraviolet lamp fixture 84 reaches an end of the filter medium 28, a limit switch 94 is tripped. The motor control 80 (See FIG. 7) senses the tripping of limit switches 94 and reverses the direction of operation of drive means 50 to reverse the direction of travel of the ultraviolet lamp fixture 84. As noted above, the lamp 34 is driven across the surface of the filter medium 60 by a drive means 50 which turns a drive gear 98 that rotates a threaded drive rod 66. The driven rod 66 threadedly engages a rigid drive bracket 100 affixed to a center of a top of lamp fixture 84. As the rod 66 is rotated the ultraviolet lamp fixture 84 is driven across the filter surface. The actuation of drive means 50 is controlled by the motor control 80 (See FIG. 7). The motor control 80 may be one of a simple timer which switches the motor on at timed intervals, a rheostat, or an intelligent integrated circuit which monitors variables such as humidity, temperature and/or air pollution to determine an optimal rate of travel for the ultraviolet lamp fixture 84. Optionally, motor control 80 may accept manual input so that the rate of travel of ultraviolet lamp fixture 84 can be set in accordance with predetermined calibrations experimentally established as optimal for destroying a specific type or class of microorganism.

As noted above, in order to prevent the electrical cord 70 from being dragged across the filter surface or becoming entangled with the ultraviolet lamp fixture 84, the cord is preferably maintained under a minimal tension by a spring-loaded take-up reel 72, or the like. The cord is supported on the lamp fixture end by a spring steel support wand 102. The cord 70 may be alternatively supported along an outer side of support rail 64 with drape hooks (not illustrated) or the like.

As noted above, the germicidal air filters 20 in accordance with the invention are preferably electrostatically enhanced so that they capture a maximum amount of particulate from filtered air. In the embodiment shown in FIG. 7, a pad of fiberglass or the like is supported over a woven screen or expanded metal mesh which serves as a grounded charging medium 32 for the filter. The charging medium 32 is connected to the negative pole of high voltage power supply 82 by a ground connection 89 (See FIG. 10). The positive pole of power supply 82 is connected to a high voltage electrode 83 that is driven through the surface of filter medium 28 to contact the positive charging medium 110 which is thereby charged with a high voltage positive charge. The high voltage electrode 83 is coated with an insulating material 112 except on an end which pierces the filter medium 28. When electrical current is supplied to the high voltage power supply 82, an electrostatic field is generated between and around the charging media 30, 32. This electrostatic field polarizes the fibers of filter medium 28 and greatly enhances the capture rate of particulate matter from air passed therethrough. Depending on the size and surface area of the filter medium 28, two or more ultraviolet lamp fixtures 84 may be connected in tandem and driven across the surface in unison. One or more lamps (not illustrated) may also be mounted on the downstream side of filter medium 28 in order to expose microorganisms to ultraviolet radiation even if they penetrate well into the filter medium.

FIG. 9 shows a schematic diagram of ultraviolet lamp fixture 84 to illustrate the effect of reflector 88 which serves the dual purpose of reflecting radiation generated by the ultraviolet lamp 34 downwards onto filter medium 28 and deflecting particle laden air to be filtered 26, away from the ultraviolet lamp 34. The air streams 26 are deflected to opposite sides of the reflector 88. Without the reflector 88, eddies (not illustrated) in the air stream would be created on each side of the ultraviolet lamp fixture 84, thus continuously flooding opposite sides of the lamp 34 with particle laden air. The ultraviolet lamp 34 generates an electrostatic charge while operating and is therefore prone to attract particulate matter. The reflector 88 deflects air streams 26 away from the lamp 34 and into filter medium 28. This creates a partial vacuum under the reflector 88. Filtered air 29 is slowly drawn by the partial vacuum up through filter medium 28 and out each side between the reflector 88 and the filter medium 28. Since the particles trapped in the filter medium 28 are held by an electrostatic attraction, the filtered air 29 drawn up through the filter by the vacuum created under the reflector 88 is substantially clean and the ultraviolet lamp 34 remains dust free for relatively long periods of time, sustaining germicidal effect and reducing the requirement for servicing of the lamp.

Figure 10:
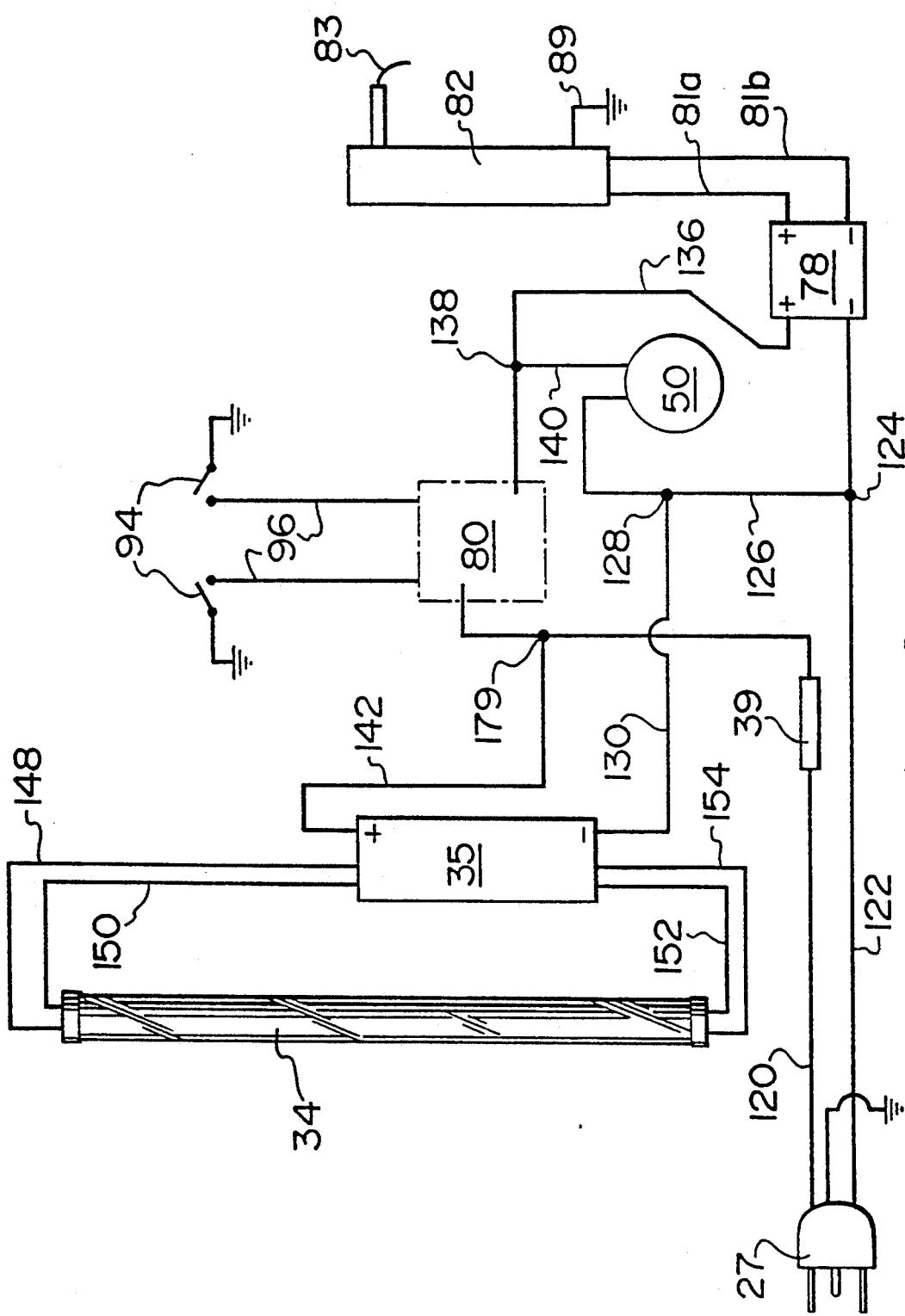
FIG. 10 is a schematic electrical wiring diagram for the germicidal air filter shown in FIG. 7.

FIG. 10 shows a simple wiring diagram for the embodiment of the invention shown in FIGS. 7 through 9. A three pronged connector 27 includes conductor 120 which connects to a fuse 39 to protect the circuitry from power surges and the like. The three pronged connector 27 also includes conductor 122 which is connected to the negative pole of the 24 volt transformer 78 and a junction point 124. A conductor 126 connects the junction point 124 and the drive means 50. A conductor 130 connects the junction point 128 to the negative pole of a ballast 35 for the ultraviolet lamp 34. Conductors 81a and 81b connect the 24 volt transformer 78 to the high voltage power supply 82. The positive pole of transformer 78 is connected by a conductor 136 to motor control 80. A conductor 175 connects a junction point 174 to drive means 50. A pair of conductors 96 connect motor control 80 and the limit switches 94. A conductor 142 connects a junction point 179 and the positive pole of the ballast 35 for ultraviolet lamp 34. Conductors 148, 150, 154 and 186 connect the output of ballast 35 to the ultraviolet lamp 34. Other wiring schemes may be used to power the germicidal air filter 20 shown in FIGS. 7 through 9.

FIG. 11 shows an exploded perspective view of a third embodiment of a germicidal air filter in accordance with the invention. This embodiment is designed for installation in a circular or rectangular air duct of an air handling system. As shown in FIG. 11, a rectangular air duct 148 accommodates a frame 150 for supporting a germicidal air filter, generally indicated by reference 20. The germicidal air filter 20 includes an ultraviolet radiation unit 152 and an air filtration unit 154. Air filtration unit 154 supports a filter medium 28 traversely in the air duct 148 so that air drawn through the duct passes through the filter medium 28. The air filtration unit 154 is preferably an electrostatically enhanced air filtration unit such as described in reference to FIGS. 1 and 8. The air filtration unit 154 is electrostatically charged by a high voltage power supply 82. The air duct 148 preferably includes a slot 156 which slideably accommodates the air filtration unit 154 so that the filter medium 28 may be replaced by sliding the air filtration unit 154 out of the air duct 148. Air to be filtered, indicated by arrows 26 enters an upstream side of the germicidal air filter 20 and is drawn through the filter medium 28 by an air handling system. The air to be filtered may be charged with ozone by one or more corona wires 151. The ozone promotes oxidation and thereby enhances the germicidal effect of the air filter. The corona wires 151 are advantageously supplied with high voltage, low amperage current by a high voltage power supply 224 (see FIG. 16). The power supply 224 is preferably housed in the housing for the power switch 160. The corona wires 151 are mounted to a bottom of the duct by an electrically insulated bottom mount 153 which includes an electrical lead (not illustrated) for supplying high voltage, low amperage electrical power to the corona 151 wire in a manner well known in the art. The corona wires are supported on their top ends by hooks 155 which are electrically insulated from the top of the air duct 148.

The upstream side of the air filter unit 154 is exposed to ultraviolet radiation by the ultraviolet radiation unit 152, the construction of which will be explained with references to FIGS. 12 through 15. The ultraviolet radiation unit 152 is supported in the air duct 148 by a support bracket 158 which is attached to opposite sides of the frame 150. The operation of the germicidal air filter 20 is controlled by an electrical switch 160 which is preferably mounted on an outside of the air duct 148. The switch 160 also preferably serves as a housing for electrical lamp ballast 35 and the 24 volt transformer 78 (see FIG. 16).

FIG. 12 shows an exploded view of a typical drive mechanism for the ultraviolet radiation unit 152. An ultraviolet lamp fixture 84 is supported on a shaft 164 which is rotatably supported by a pillow block 166. The shaft 164 is turned by a drive means 50 which may be a stepper motor, a geared motor or the like. The ultraviolet lamp fixture 84 must be supplied with electric current. A pair of brushes 86 attached to electrical conductors (not illustrated in this Figure) contact ring contactors 85 which are in turn connected to electrical conductors that power an ultraviolet lamp 34 (see FIG. 13). The ring contactors 85 are mounted on a cylindrical insulator 87 preferably made of rubber, plastic or the like. The drive motor 168, the pillow block 166, the drive shaft 164, and the electrical contactors 85 and brushes 86 are all covered by a removable hood 170 for protecting the apparatus from dust laden air.

FIG. 13 shows a side elevational cross-section of the ultraviolet irradiation unit 152. As is apparent, an ultraviolet lamp 34 is supported by a reflector 88 which surrounds the sides and rear of the lamp. The reflector 88 is connected to the shaft 164 by a thumb nut 174. Electrical conductors 148, 150, 152 and 154 pass through the shaft 164 and electrically interconnect the ring contactors 85 and the ultraviolet lamp 34.

Figure 14:
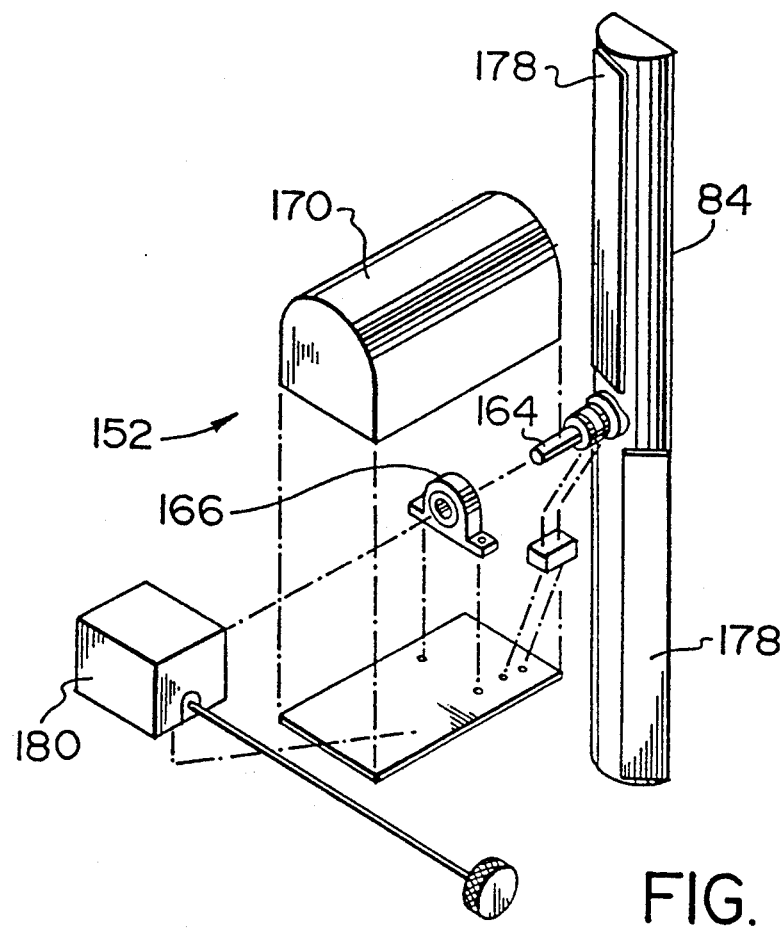
FIG. 14 is an exploded perspective view of an air powered drive arrangement for the germicidal air filter shown in FIG. 11.

FIG. 14 shows an alternate drive mechanism for the ultraviolet lamp fixture 84. In this embodiment, the lamp fixture is rotated by air to be filtered 26 which is drawn through the air duct 148 (see FIG. 11) by the air handling system. This may be accomplished by attaching blades 178 to opposite sides of a rear surface of the lamp fixture 84. The blades are oriented at opposite angles to provide a propeller-shaped drive mechanism. Alternatively, a propeller drive which is independent of the lamp fixture 84 can be mounted to the shaft 164. The shaft 164 is rotatably supported by the pillow block 166. The speed of rotation is controlled by a friction clutch 180, the construction of which is explained with reference to FIG. 15. All other components of the ultraviolet radiation unit 152 are identical to those described with reference to the embodiment shown in FIG. 13.

Figure 15:
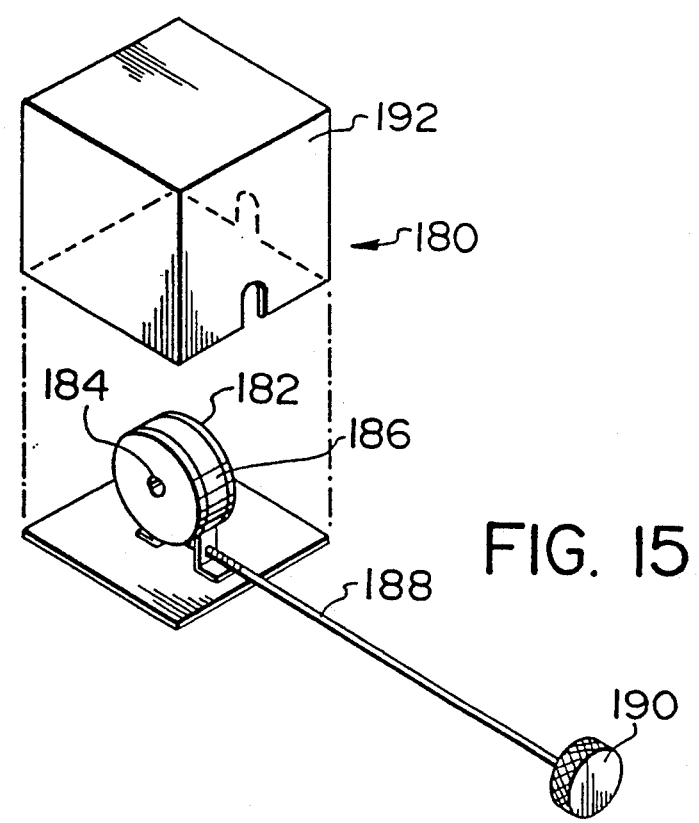
FIG. 15 is a detailed perspective view of a friction clutch for controlling the rotational speed of the drive arrangement shown in FIG. 14.

FIG. 15 is a perspective view of the friction clutch 180 which is used to control the rotational speed of the air driven ultraviolet lamp fixture 84 shown in FIG. 14. The friction clutch 180 includes a compressible disk 182 having an axial bore 184 in which the shaft 164 (see FIG. 14) rotates. A resilient band 186 surrounds a circumference of the compressible disk 182. The diameter of resilient band 186 may be selectively adjusted by turning a threaded rod 188, having a knurled knob 190 on its outer end. Rotating the knob 190 in a clockwise direction decreases the diameter of the resilient band 186 and compresses the disk 182 so that the bore 184 tightens on the shaft 164 and thereby controls the rotational speed of the ultraviolet lamp fixture 84 which supports the ultraviolet lamp 34 (see FIG. 13). The friction clutch 180 preferably includes a hood 192 for protecting the mechanism from air borne particulates.

Figure 16:
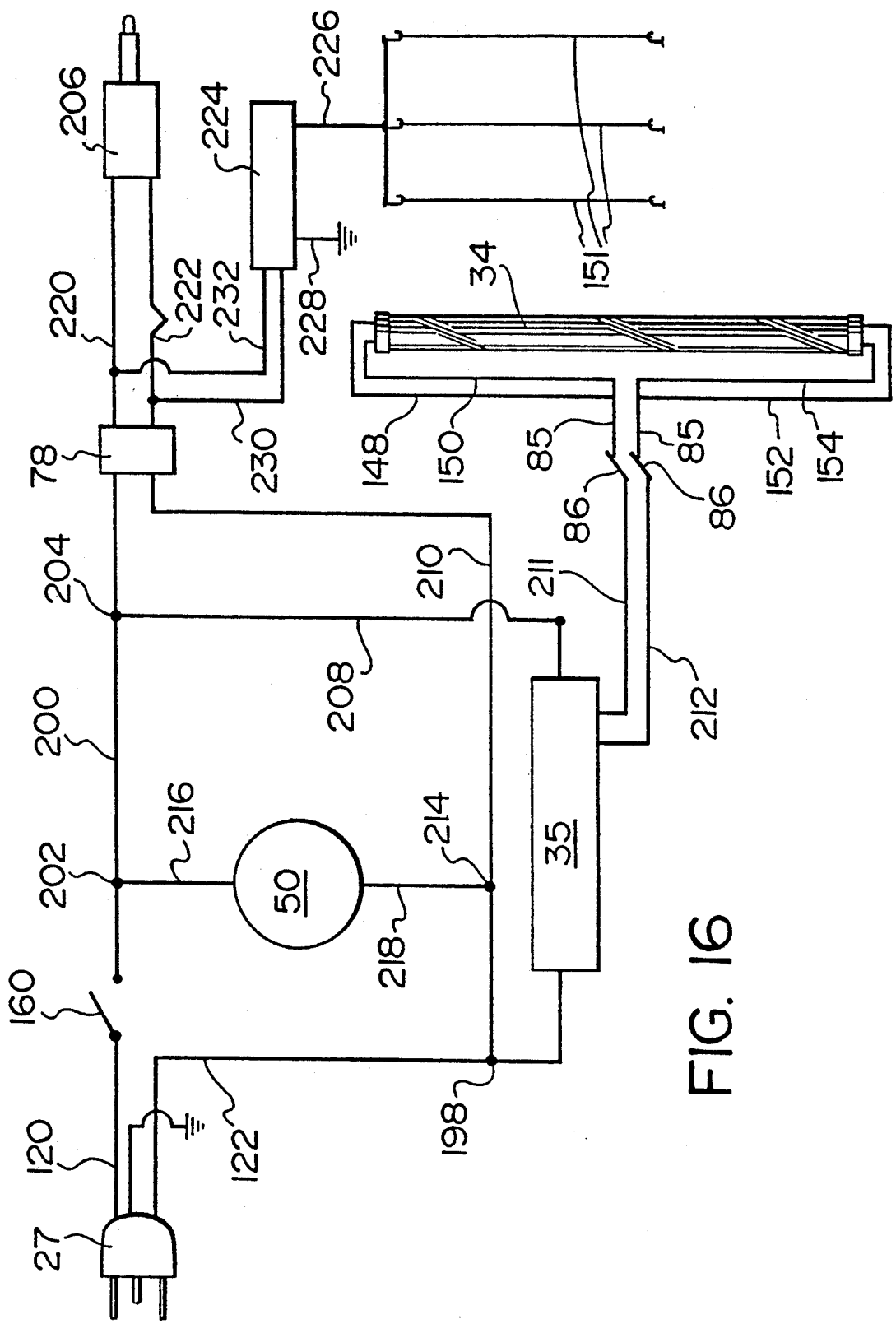
FIG. 16 is a schematic electrical wiring diagram for use with the germicidal air filter shown in FIG. 12.

FIG. 16 shows a schematic electrical diagram suitable for use with the embodiment of the invention shown in FIGS. 11-13. The circuit may include a three prong electrical connector 27 or it may be connected directly to mains power using a junction box (not illustrated). A conductor 120 is connected with the electrical switch 160. A second electrical conductor 122 is connected to a junction point 198 and the ballast 35 for powering the ultraviolet lamp 34. An electrical conductor 200 connects the switch 160 with a junction point 202, a junction point 204 and the 24 volt transformer 78. A second conductor 208 connects the junction point 204 with the ballast 35 for the ultraviolet lamp 34. An electrical conductor 216 connects a junction point 202 with the drive means 50. A second electrical conductor 218 connects a junction point 214 with the opposite side of the drive means 50. Conductors 211 and 212 conduct electrical current from the ballast 35 to the brushes 86 which contact the ring contactors 85 (see FIG. 13). Electrical conductors 148, 150, 152 and 154 conduct electrical current from the ring contactors 85 to the ultraviolet lamp 34. Conductor 220 connects the positive pole of the transformer 78 to a bipolar electrical Jack 205 and a conductor 222 connects the neutral pole of the 24 volt transformer 78 with the bipolar electrical Jack 206. The bipolar electrical jack 206 is used to supply the high voltage power supply 82 (see FIG. 11) with 24 volt current from transformer 78. Conductors 230 and 232 connect the respective output poles of the transformer 78 to the corresponding input poles of second high voltage power supply 224 which is required if corona wires 151 are a port of the germicidal air filter. The positive output pole of the high voltage power supply 224 is connected to a conductor 226 which supplies high voltage, low amperage power to the corona wires 151. The negative pole of the high voltage power supply is connected to a ground 228.

Figure 17:
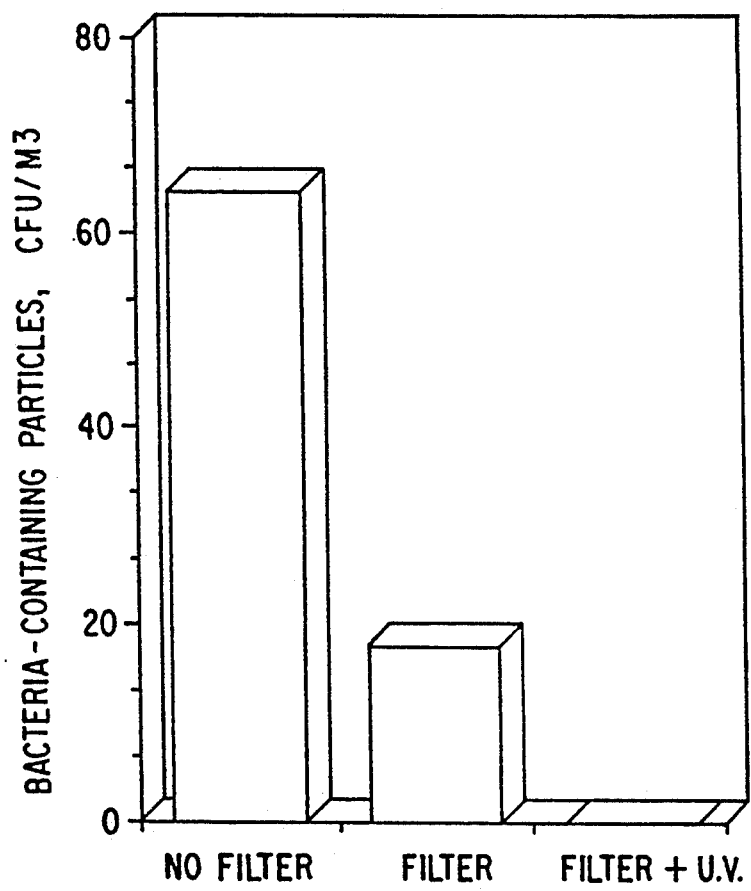
FIG. 17 is a bar graph showing the effects of an electrostatically enhanced germicidal air filter on airborne bacterial colony forming units in an enclosed test chamber.

FIG. 17 shows a bar graph of the effect of two air filter constructions on a count of airborne bacteria-containing particles suspended in a test chamber. The horizontal axis of the bar graph shows test results for bacteria counts taken in a 70 cubic foot test chamber with no filtration, an electrostatically enhanced air filter and an electrostatically enhanced germicidal air filter in accordance with the invention. The vertical axis shows the number of bacteria-containing particles collected in a controlled sample taken from the air of the chamber. Without filtration approximately 65 bacteria-containing particles were collected in the control sample as established by a bacterial culture on agar agar in a petri dish. After five minutes with an electrostatically enhanced air filtration unit operating at a 200 feet per minute air velocity across the filter and 400 cubic feet per minute filtration rate at a temperature of 65° F. in a relative humidity of 50% approximately 18 bacteria-containing particles were collected in the controlled sample culture in the manner described above. Using the same bacterial concentration and the same filtration rate, the test chamber was effectively ridded of airborne bacteria-containing particles by a germicidal air filter in accordance with the invention. After five minutes of filtration no bacteria-containing particles could be detected in the test chamber using the method described above. It is therefore apparent that the germicidal air filters in accordance with the invention are extremely effective in removing and destroying airborne microorganisms from air which is filtered.

INDUSTRIAL APPLICABILITY

It is well established that airborne microorganisms account for a spread of infection, especially in hospital and medical institutions where large numbers of infected and/or susceptible individuals are concentrated. This problem has been exacerbated in recent years by a growing population of immune deficient individuals, principally those who have contracted Acquired Immune Deficiency Syndrome (AIDS).

There therefore exists a need for an air purification system which is capable of effectively destroying airborne microorganisms and thereby controlling the spread of infectious diseases by airborne carriers. The germicidal air filters in accordance with the invention provide apparatus which are effective at controlling or eliminating airborne microorganisms from a confined environment. They may be used to construct units which purify the air in a single room or an entire institution. The units are effective, safe to operate and relatively simple to manufacture.

It is apparent from the foregoing that a substantial advance in air handling equipment has been invented. To those skilled in the art, changes and modifications to the specific embodiments of the invention described above will be apparent. The specific embodiments described are intended to be exemplary only, the scope of the invention being limited solely by the scope of the appended claims.

We claim:

1. A germicidal air filter, comprising:
    a filter medium for removing particulate matter including at least a portion of microorganisms from an air stream to be filtered, the filter medium having an upstream side exposed to the air to be filtered;
    an ultraviolet radiation source located in proximity of the upstream side of the filter medium for exposing at least a portion of that side of the filter medium to ultraviolet radiation at germicidal levels;
    one of said radiation sources and filter medium being displaceable with respect to the other of the radiation source and the filter medium; and
    means for displacing said one radiation source and filter medium so that a surface of the upstream side of the filter medium is systematically and repeatedly exposed to germicidal levels of radiation.

2. A germicidal air filter as claimed in claim 1 wherein the filter medium comprises a cylindrical filter medium having a longitudinal axis, and the filter medium is rotated about the axis in a proximity of the ultraviolet radiation source so that the upstream side of the filter medium is systematically and repeatedly exposed to germicidal levels of radiation.

3. A germicidal air filter as claimed in claim 1 wherein the filter medium includes a planar filter medium disposed in an air handling system, and the ultraviolet radiation source is moved reciprocally across the upstream side of the filter medium to systematically and repeatedly expose the upstream side of the filter medium to germicidal levels of ultraviolet radiation.

4. A germicidal air filter as claimed in claim 1 wherein the filter medium is a planar filter medium disposed in an air duct of an air handling system and the ultraviolet radiation source is rotated in close proximity to the upstream side of the filter medium about an axis which is oriented at a right angle with respect to a longitudinal axis of the radiation source so that a circular area of the upstream side of the filter medium is systematically and repeatedly exposed to germicidal levels of ultraviolet radiation.

5. The germicidal air filter as claimed in claim 4 wherein the radiation source is moved by an electric motor which drives a shaft that supports the radiation source.

6. The germicidal air filter as claimed in claim 4 wherein the radiation source is moved by an action of air movement through the air duct on propeller-shaped blades affixed to a shaft which supports the radiation source.

7. The germicidal air filter as claimed in claim 6 wherein a speed of rotation of the radiation source is controlled by a friction clutch mounted to the shaft.

8. A germicidal air filter as claimed in claim 1 wherein the filter medium is a fibrous filter medium.

9. The germicidal air filter as claimed in claim 8 wherein the fibrous filter medium is electrostatically enhanced so that the fibers of the filter are polarized by an electrostatic field to increase the efficiency of the filter medium in capturing particulate matter suspended in air to be filtered.

10. The germicidal air filter as claimed in claim 9 wherein the filter medium is a pleated paper medium suitable for use in filtering air.

11. The germicidal air filter as claimed in claim 9 wherein the filter medium is a fiberglass medium suitable for use in filtering air.

12. The germicidal air filter as claimed in claim 1 wherein the ultraviolet radiation source is an ultraviolet lamp.

13. The germicidal air filter as claimed in claim 12 wherein the ultraviolet lamp is an ozone producing lamp.

14. The germicidal air filter as claimed in claim 1 wherein the ultraviolet radiation source is shielded from a direct contact with air to be filtered in order to inhibit an accumulation of particulate matter on a surface of the radiation source, which particulate matter could absorb and reflect ultraviolet radiation and thereby inhibit a germicidal effect of the radiation source.

15. The germicidal air filter as claimed in claim 1 further including at least one ultraviolet radiation source located in proximity of a downstream side of the filter medium for exposing at least a portion of said side of the filter medium to ultraviolet radiation.

16. The germicidal air filter as claimed in claim 1 further including at least one corona wire located on the upstream side of the filter medium for generating ozone to promote oxidation and thereby enhance the germicidal effect of the air filter.

17. A germicidal air filter comprising:
 a cabinet having louvers for admitting air to be filtered and louvers for exhausting filtered air from the cabinet;
 a filter medium arranged in a hollow cylindrical configuration and having a longitudinal axis, the filter medium being mounted within the cabinet for rotation about its longitudinal axis;
 an ultraviolet lamp mounted adjacent an outer side of the filter medium;
 means for rotating the filter medium about the longitudinal axis;
 a fan for moving air to be filtered through the louvers for admitting air to be filtered, the outer side of the filter medium and the louvres for exhausting filtered air;
 whereby airborne microorganisms suspended in air to be filtered are trapped by the filter medium and exposed to a lethal dose of radiation when the rotation of the filter medium moves the trapped microorganisms into a proximity of the ultraviolet lamp.

* * * * *